United States Patent [19]

Grendahl

[11] Patent Number: 4,906,246
[45] Date of Patent: * Mar. 6, 1990

[54] CYLINDRICALLY SEGMENTED ZONE OF FOCUS ARTIFICIAL HYDROGEL LENS

[76] Inventor: Dennis T. Grendahl, 2070 Shoreline Dr., Orono, Minn. 55422

[*] Notice: The portion of the term of this patent subsequent to Jan. 3, 2006 has been disclaimed.

[21] Appl. No.: 258,027

[22] Filed: Oct. 17, 1988

Related U.S. Application Data

[63] Continuation-in-part of Ser. No. 88,413, Aug. 24, 1987, Pat. No. 4,795,462.

[51] Int. Cl.⁴ .............................................. A61F 2/16
[52] U.S. Cl. ................................................... 623/6
[58] Field of Search .............................. 623/6; 351/161

[56] References Cited

U.S. PATENT DOCUMENTS

| | | | |
|---|---|---|---|
| 4,240,163 | 12/1980 | Galin | 623/6 |
| 4,655,565 | 4/1987 | Freeman | 623/6 |
| 4,666,446 | 5/1987 | Koziol | 623/6 |
| 4,704,016 | 11/1987 | de Carle | 351/161 |
| 4,795,462 | 1/1989 | Grendahl | 623/6 |

FOREIGN PATENT DOCUMENTS

| | | | |
|---|---|---|---|
| 162573 | 11/1985 | European Pat. Off. | 623/6 |
| 8603961 | 7/1986 | PCT Int'l Appl. | 623/6 |
| 2181355 | 4/1987 | United Kingdom | 623/6 |

Primary Examiner—Richard J. Apley
Assistant Examiner—James Prizant
Attorney, Agent, or Firm—Hugh D. Jaeger

[57] ABSTRACT

An implantable or contact hydrogel lens for replacement of a defective natural lens in an eye in which various annular portions of the lens have different powers and focal lengths to produce in-focus images, on different portions of the retina, of objects which are located at various distances from the eye, thereby substituting for the natural focusing action of the eye. The image processing capability of the brain functions to largely ignore the out of focus images and concentrate on the in focus image of the object selected by the brain for consideration.

19 Claims, 9 Drawing Sheets

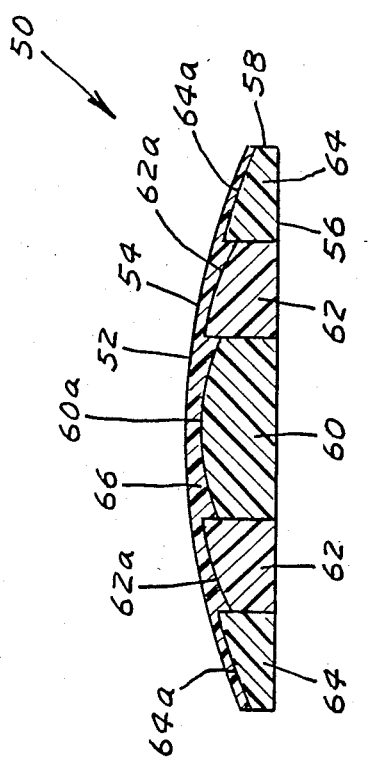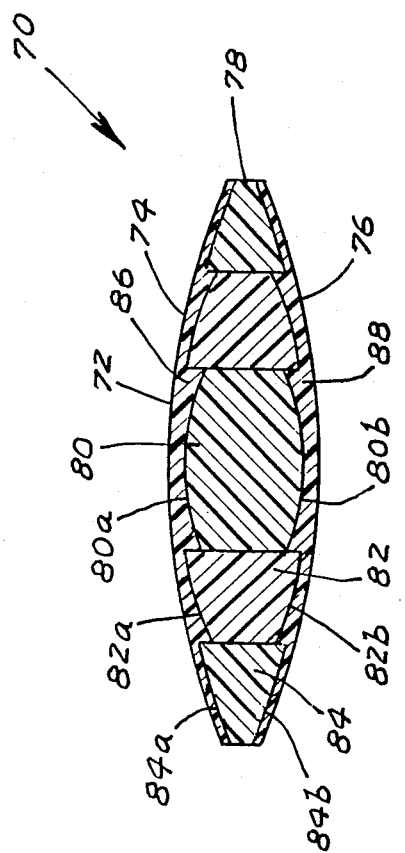

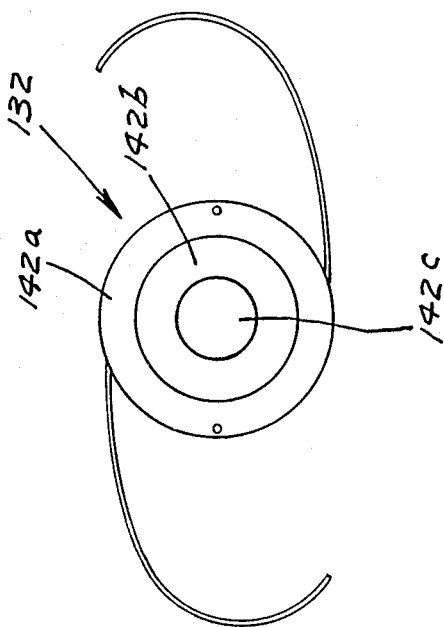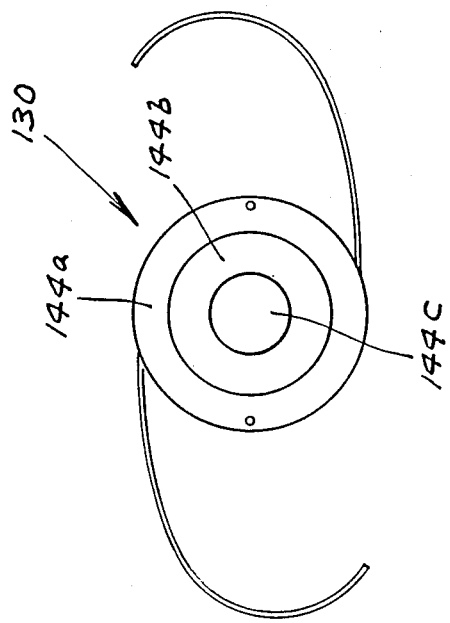
FIG. 10

CYLINDRICALLY SEGMENTED ZONE OF FOCUS ARTIFICIAL HYDROGEL LENS

This application is a Continuation-in-Part of Application Ser. No. 07/088,413, filed Aug. 24, 1987, entitled "Cylindrically Segmented Zone of Focus Artificial Lens", now U.S. Pat. No. 4,795,462; which is related in part to Application Ser. No. 07/258,028, filed Oct. 17, 1988, entitled "Laminated Zone of Focus Artificial Hydrogel Lens", which is a Continuation-in-Part of Application Ser. No. 07/088,428, filed Aug. 4, 1987, entitled "Laminated Zone of Focus Artificial Lens", now U.S. Pat. No. 4,798,609; which is related in part to Application Ser. No. 07/258,019, filed Oct. 17, 1988, entitled "Multiple Element Zone of Focus Artificial Hydrogel Lens", which is a Continuation-in-Part of Application Ser. No. 07/088,412, filed Aug. 24, 1987, entitled "Multiple Element Zone of Focus Artificial Lens", now U.S. Pat. No. 4,778,462; and Application Ser. No. 07/258,029, filed Oct. 17, 1988, entitled "Radially Segmented Zone of Focus Artificial Hydrogel Lens", which is a Continuation-in-Part of Application Ser. No. 07/088,249, filed Aug. 24, 1987, entitled "Radially Segmented Zone of Focus Artificial Lens", now U.S. Pat. No. 4,798,609.

BACKGROUND OF THE INVENTION

1. Field of the Invention

The present invention pertains to an implanatable intraocular lens, and more particularly, pertains to a hydrogel lens containing annular lens elements. The present invention relates to hydrogel lenses which have discrete areas which serve to bring impinging rays to a focus in an specific area of the focal plane. Such lenses are called zone of focus lenses and are particularly useful for implantation into the eye as a substitute for the natural lens since, in combination with the brain, they effectively replicate the ability of the natural lens to bring objects at varying distances to a sharp focus.

The invention relates specifically to a zone of focus lens in which the hydrogel lens is divided into annular lens elements. Each lens element serves to bring the impinging rays from an object at a predetermined distance to a focus on a particular region of the retina. By selecting various powers for the hydrogel lens elements, it is possible to have an object at a given distance brought to an acceptable focus by at least one of such elements. In this manner, an in-focus image (sharp image) is created on a particular portion of the retina serviced by that element. It has been found that the processing of the image by the brain results in the selective consideration of the sharpest image and the virtual discard of the other out of focus images created by other elements.

2. Description of the Prior Art

Prior art includes limited attempts to produce a lens having areas of varying powers have been made. There have been many attempts to produce implantable lenses which serve for both close and far seeing, similar to the bifocal spectacles. In general, such lenses have been produced with two regions having different powers. The light which impinges on the retina passes through one region to the exclusion of the other. In such a system, only one region of the lens is used at a time and there is no accommodation by the brain to reject an out of focus image. Great care and accuracy must be used in the pre-operative measurements since both the near and far powers must be accurately determined. Since the near and far powers are not specifically interrelated, the inventory requirements are compounded since a variety of near powers must be available for every far power.

Further, the rigid materials used for lenses have required relatively large incisions for implantation, but the post-operative recovery period is shorter when a small incision is made.

The present invention overcomes the disadvantages of prior art references by providing a hydrogel lens capable of implantation through a small incision, which includes an annularly segmented lens where each segment is of a different power.

SUMMARY OF THE INVENTION

The hydrogel lens is a composite of a cylindrical and annular optical lens elements, each of which has a distinct power and focal length. Each element brings the impinging rays to bear on a predetermined portion of the retina, which may be either unique to that element or shared with other elements of like power. The hydrogel lens elements are selected to have a sufficient range of powers to accommodate the projected use. That is, the value of the power and the number of elements will be determined by the projected use. Most uses can be accommodated with a lens having two or three powers to accommodate objects at near, far and intermediate distances. These powers can be distributed among a like number of lens elements or a number of elements which is two, three or even more times the number of powers. The distribution of powers among the elements need not be done equally. For example, if most of the sight is required at close distances, the number of elements for this distance can be increased and the number of elements for far vision correspondingly decreased. Alternatively, the various elements may have different areas.

Accommodation of the brain to such an arrangement may be enhanced by adding a distinctive color to the elements of like power. This approach may be utilized where loss or impairment of color vision is of little consequence.

Hydrogel lens elements of differing powers can be provided by grinding or otherwise forming a uniform lens surface over a composite structure of hydrogel elements having differing indices of refraction.

In the alternative, the lens elements can be fabricated of like hydrogel material and the differing powers obtained by grinding, molding or otherwise shaping the surface of the individual elements to provide individual curvatures.

Lens is a generic term for intraocular lens, intracorneal lens, or contact lens. Lenses also include any optical lens such as a camera, television, telescopes, projectors, optical instruments, glasses, etc.

It is a principal object hereof to provide an intraocular hydrogel lens including a cylindrically segmented zone of focus artificial lens optic.

It is another object of the invention to provide a minimum cost zone of focus hydrogel lens which does not require either an extensive inventory of various powers and combination of powers or extensive preoperative measurement prior to implantation into the eye as a replacement for a defective lens.

Still another object of this invention is to provide a very low cost approach to the replacement of a defective lens by providing a very nearly universal hydrogel lens which provides vision adequate to allow a normal life style.

These lenses can be used as replacements for the presbyoptic lens of the aging population and thereby allowing for both near and distant vision without the use of spectacles. Intraocular lenses sometimes become decentered. Distant and near vision with this zone of focus lens will not be affected by decentration.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4 illustrates a cross-sectional view of FIG. 1;

FIG. 5 illustrates a cross-sectional view taken along line 5—5 of FIG. 1;

FIG. 10 illustrates a plan view of a pair of cylindrically segmented zone of focus hydrogel lenses for use in the left and right eyes of a patient; and, FIGS. 11, 12 and 13 are illustrative examples of multiple element embodiments in which the annular elements are so thin as to lead to reflections from the walls.

DESCRIPTION OF THE PREFERRED EMBODIMENTS

Figure 1:
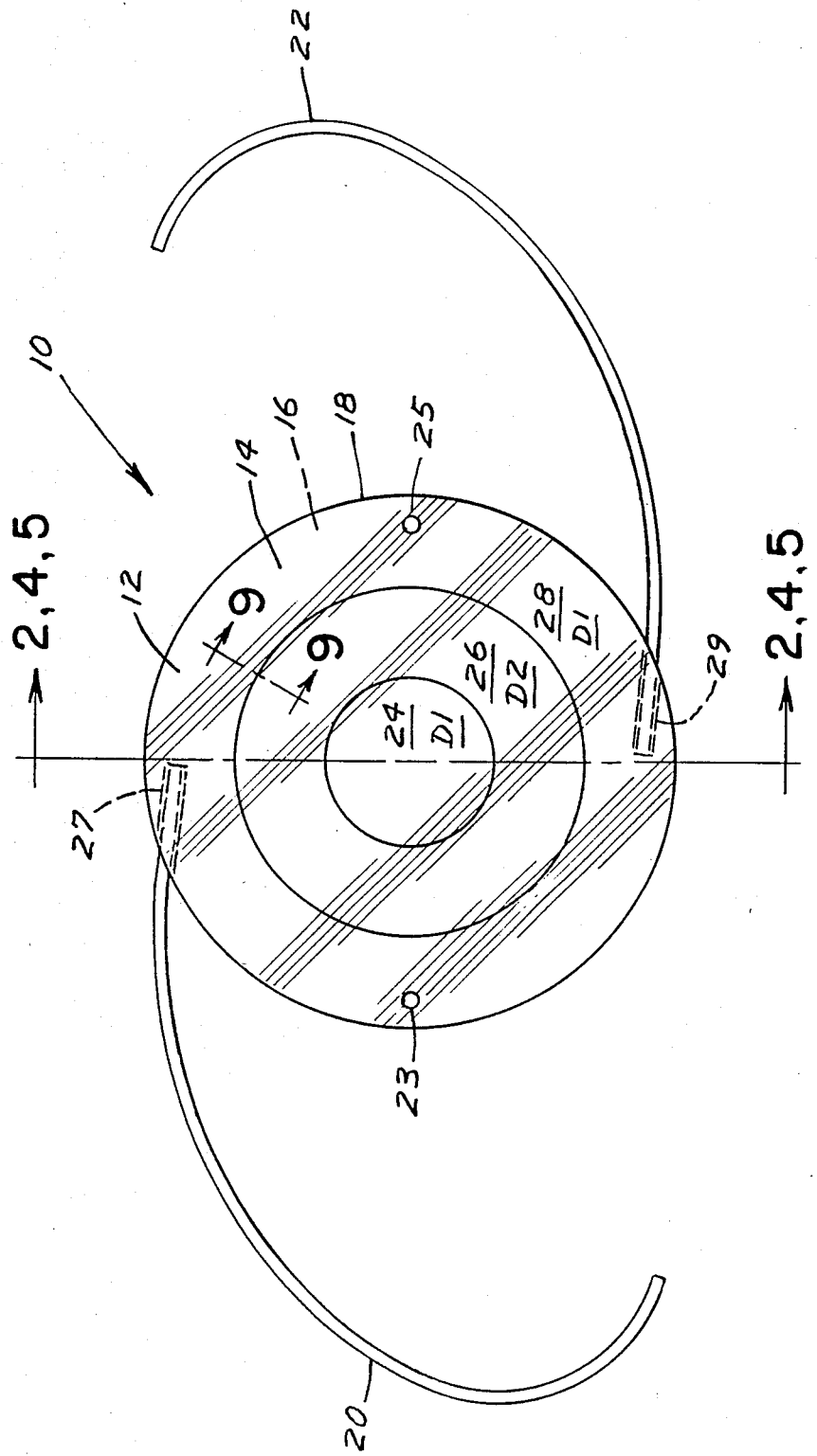
FIG. 1 illustrates a top view of a cylindrically segmented zone of focus hydrogel lens according to the invention.

FIG. 1 illustrates a top view of a cylindrically segmented zone of focus artificial lens 10, of hydrogel material, includes an optic 12, an anterior surface 14, posterior surface 16, an edge 18, open loop haptics 20 and 22 for fixation of the lens to the interior of the eye and positioning holes 23 and 25. Open loop haptics 20 and 22 secure into holes 27 and 29 by known processes. The shape of lens 10 may be varied to accommodate optical or other requirements. The lens 10 is primarily illustrated as a plano-convex lens, but can assume any other convenient shape such as meniscus, biconvex, or any other desired lens shape. The lens 10 has a central cylindrical element 24 and a plurality of concentric annular elements 26 and 28. Each of the elements 24, 26 and 28 may have a distinct focal length or power so as to bring objects of differing distance into focus on different area of the common focal plane. In general, it will be found that two or three powers will be optimum in terms of performance within the human eye. A larger number of powers may not provide adequate sharp images for consideration by the brain and more powers will add to the cost and may unduly complicate the process of adaption by the patient. With two different powers, the elements of like power can be interspersed with elements of the other powers. Alternatively, elements of like power may be located in the regions where adaptation is facilitated. Further alternatives include locating the elements, and the image they produce, in accordance with physical characteristics of the eye itself to accommodate retinal or corneal defects. While three lens elements are shown in the embodiment of FIG. 1 it will be appreciated that the invention is not so limited, and a different number of elements is permissible.

The power of the individual elements is determined by their radius of curvature and the index of refraction, either of which may be varied to provide the desired power. In the embodiment of FIG. 1, the radius of curvature for all elements at the anterior surface is the same and the index of refraction of the hydrogel material is varied to provide the necessary difference in power. The index of refraction can be modified by changing the molecular length of the polymer while maintaining compatibility with the other characteristics or by the introduction of suitable additives.

Fabrication of lens 10 may begin with the creation of a composite rod or similar structure in which the cross section of the rod resembles the plan view of FIG. 1. Such a rod can be made by simultaneous extrusion of the elements from differing material or by individual extrusion or other shaping and subsequent joining of the elements. While the extrusion process has certain advantages, particularly that of low cost, the individual fabrication of the elements and subsequent joining affords the opportunity to coat the interceding junctions of annular concentric or central elements with an anti-reflection coating or otherwise mask it, as later described in detail. In either case, the resulting blank may be sliced and fabricated into lenses either by further molding in a die which has the radii of curvature for the desired optical characteristics, by conventional lathe cutting, or other similar optical finishing techniques.

Figure 2:
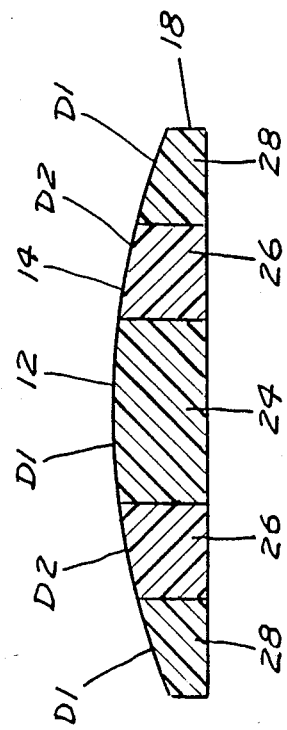
FIG. 2 illustrates a cross-sectional view taken along line 2—2 of FIG. 1.

FIG. 2 illustrates a cross-sectional view taken along line 2—2 of FIG. 1 where all numerals correspond to those elements previously described.

Figure 3A:
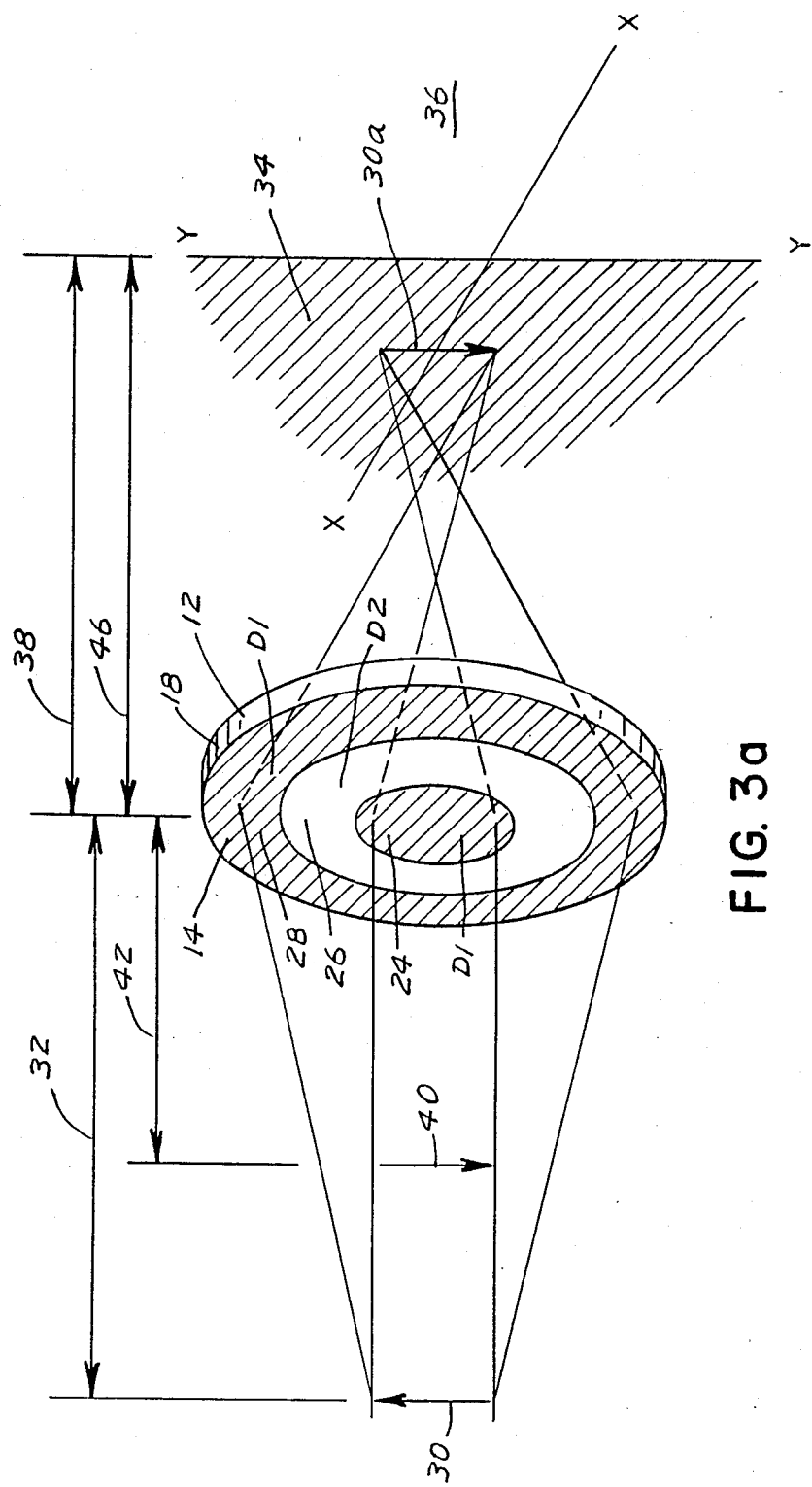
FIGS. 3A and 3B illustrate a schematic isometric view of an optical system in which the zone of focus hydrogel lens develops individual images for each lens element.
Figure 3B:
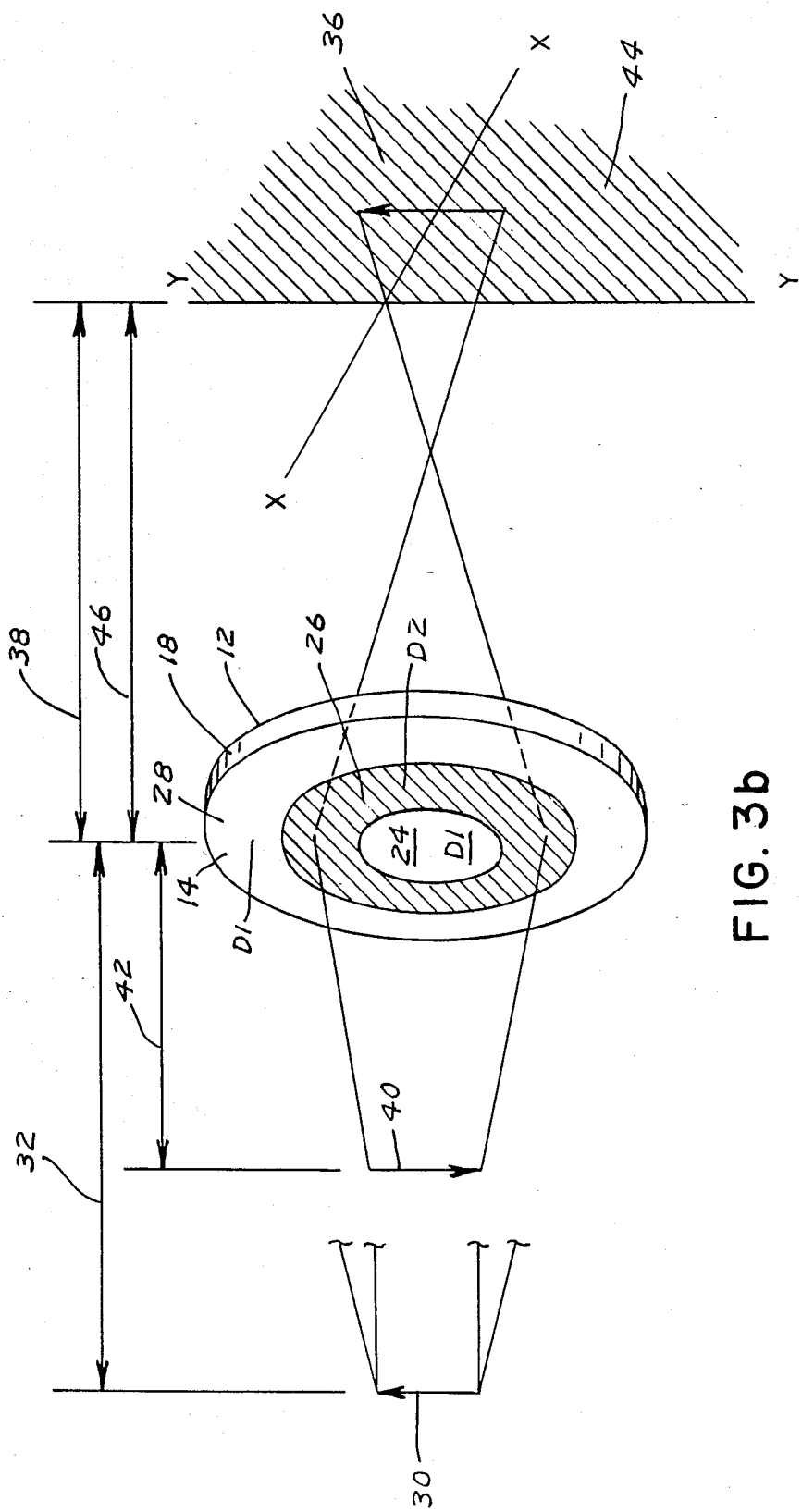

FIGS. 3A and 3B illustrate a schematic view of an optical system utilizing the lens of FIG. 1 where all numerals correspond to those elements previously described. Haptics 20 and 22 are not shown for purposes of brevity and clarity of the illustration. In FIG. 3A the elements 24 and 28 have a common power D1 and bring a far object 30 located at a far distance 32 to focus on a focal area 34 lying in a configured retinal focal plane 36 as indicated by an x-y axis at a far focal distance 38, the distance between the optic 12 and configured retinal focal plane 36 which terminates at the configured retinal focal plane 36. In FIG. 3B the element 26 has a power D2 and brings a near object 40, located at a near distance 42 to focus in area 44 at a focal distance 46 also terminating at configured retinal focal plane 36. It can be seen that the elements 24 and 26-28 of lens 10 each produce an image on a distinct area. For example, elements 24 and 28 produce sharp images of far object 30 in the focal area 34 of the configured retinal focal plane 36 shown as 30a. Similarly, annular element 26 produces a sharp image of near object 40 in the area 44 of the retinal focal plane 36 shown as 40a.

It will be appreciated that the annular element 26, in addition to producing a sharp image of a near object 40, will also produce an out-of-focus image of the far object 30. Similarly, the elements 24 and 28 will simultaneously produce a sharp image of the far object 30 and an out-of-focus image of near object 40. The adaptive power of the brain effectively rejects the out-of-focus image and permits the in-focus image of the desired object to predominate. The adaptive capability varies with individuals and can sometimes be enhanced by selective positioning, sizing and coloration of the elements in accordance with personal characteristics of the individual.

FIG. 4 illustrates a sectional view along the line 4—4 of FIG. 1, representing an embodiment of a hydrogel lens 50 where the various elements are made from material having the same index of refraction. The plan view of the lens 50 is the same as for the lens 10 in FIG. 1 where the central element 24 and annular elements 26 and 28 correspond in overhead view to the corresponding elements of this FIG. The hydrogel lens 50 includes an optic 52 including a convex anterior surface 54, a planar posterior surface 56, an edge 58 therebetween, a central element 60, and concentric annular rings 62 and 64. The differing powers are provided by fabricating the lens elements with different radii of curvature. In this sectional view taken from the same aspect as FIG. 1, the curved portion 60a of the central element 60 has more curvature than the curved portion 62a of the annular element 62, representing the higher power of the former and the curved portion 64a of the annular element 64 has yet a different curvature then either curved portions 60a or 62a. Since the elements do not have a uniform curvature, conventional grinding or lathe cutting techniques may not be suitable for fabrication. It may be desirable to form the lens 10 in a die having suitable dimensions or to individually fabricate the elements and join them after at least one surface is fabricated.

Since the embodiment shown in FIG. 4 will have at least one discontinuous surface, a smooth layer 66 over the curved portions 60a, 62a and 64a to overcoat the curved surfaces will avoid irritation when the lens is implanted.

FIG. 5 illustrates a cross-sectional view of FIG. 1 taken along line 5—5 of FIG. 1, and more particularly is illustrative of an embodiment of a biconvex hydrogel lens 70 in which the posterior and anterior surfaces have layers to form smooth portions over the discontinuous surfaces of the lens where all numerals correspond to those elements previously described.

This FIG. illustrates a sectional view along line 5—5 of FIG. 1 representing an embodiment of a hydrogel lens 70 having a biconvex shape where the various elements are made of material having the same index of refraction. The plan view of the lens is the same as for the hydrogel lens 10 and 50 illustrated in FIG. 1 where the central element 24 and the annular elements 26 and 2 correspond in overhead view to correspondingly place elements of this FIG. The biconvex hydrogel lens 70 is somewhat similar to the hydrogel lens 50 with the inclusion and addition of a convex posterior side which is a mirror like image of the anterior side. The hydrogel lens 70 includes an optic 72, a convex anterior surface 74, a convex posterior surface 76, and an edge 78 therebetween. The differing powers are provided by fabricating the central and concentric annular elements with different radii of curvature. In this sectional view taken from FIG. 1, the central element 80 includes an anterior curved surface 80a and a posterior curved surface 80b, each of which has more curvature than the anterior curved portion 82a and the posterior portion 82b of the annular element 82 representing the higher power of the former. The upper curved portion 84a and the lower portion 84b of the annular element 84 has yet a different curvature than surfaces 80a-80b and 82a-82b. Since the elements do not have a uniform curvature, conventional grinding or lathe cutting techniques may not be suitable for fabrication. It may be desirous to form the lens 70 in a die having suitable dimensions or to individually fabricate the elements and join them after at least one surface is fabricated. Since the embodiment shown in FIG. 5 has two discontinuous surfaces, a top layer 86 is applied over the anterior curved surfaces 80a, 82a and 84a and a bottom layer 88 is applied over the posterior curved surfaces 80b, 82b and 84b to avoid irritation when the lens is implanted.

Figure 6:
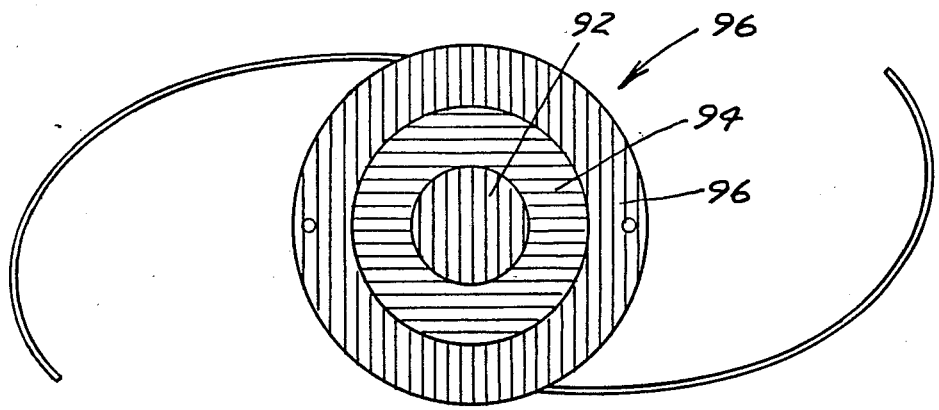
FIGS. 6, 7, and 8 illustrate plan views of an embodiment of segmented zone of focus hydrogel lens having colored elements of differing area and power.
Figure 7:
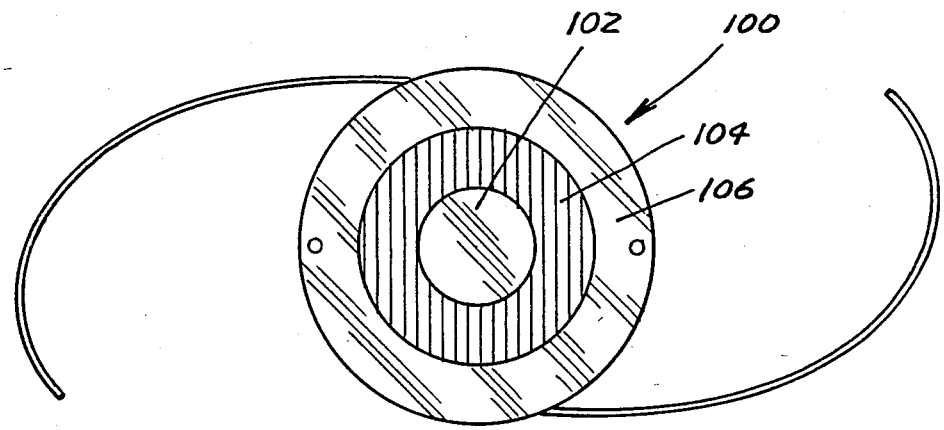
Figure 8:
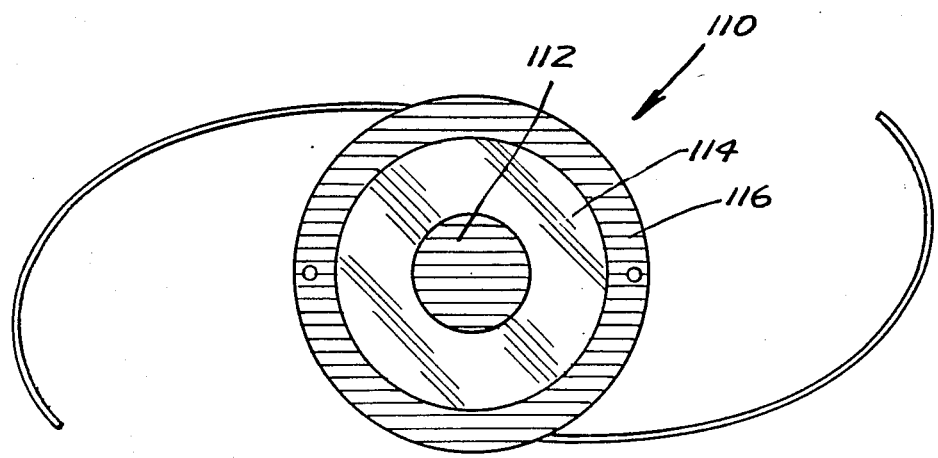

FIGS. 6, 7 and 8 illustrate alternative embodiments which may incorporate the same inventive elements similar to those found in FIGS. 1, 2, 4 and 5, and which utilize colored elements of various sizes to enhance the adaptation of the individual patient. FIG. 6 illustrates a hydrogel lens 90 including a central member 92 and concentric annular elements 94 and 96. The central member 92 and element 96 have like powers and are colored red or some other suitable color. Element 94 has a power differing from the common power of central member 92 and element 96, and is of a different suitable color such as blue. The hydrogel lens 90, central element 92, elements 94 and 96, and other elements found in FIGS. 7 and 8, are shaded accordingly with appropriate color codes. The colors assist the brain in distinguishing the images produced from the two groups of elements.

FIG. 7 illustrates a hydrogel lens 100 including a central member 102 and concentric annular members 104 and 106. Only the annular concentric element 104 is colored and the central member 102 and element 106 have like powers and are transparent. Annular element 104 is colored red for purposes of example only, but can be colored any other desired color.

FIG. 8 illustrates a hydrogel lens 110 including a central member 112 and concentric annular member 114 and 116. Annular central member 112 and element 116 have the same powers and are colored with a color such as blue, for purposes of illustration only, and the remaining annular element 114, which is larger than the sum of the areas of central member 112 and element 116, is transparent.

Figure 9:
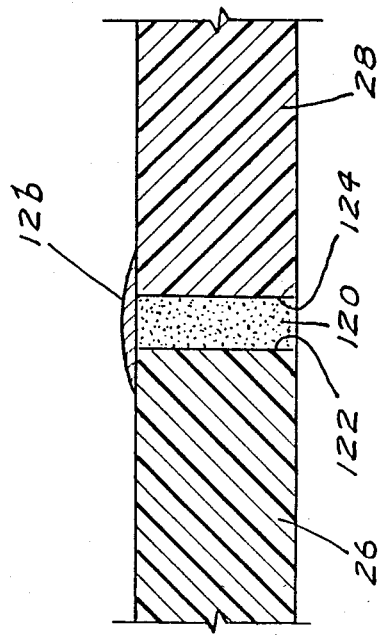
FIG. 9 illustrates a cross-sectional view of the junction between elements illustrating the anti-reflection coating and mask taken along line 9—9 of FIG. 1.

FIG. 9 illustrates a cross-sectional view of the hydrogel lens taken along the line 9—9 of FIG. to show the junction between two elements where the elements are joined subsequent to extrusion. The concentric annular element 26 is joined to element 28 by a layer of transparent adhesive material 120. The material 120 may include an additive to provide antireflection characteristics. Alternatively, a conventional, discrete, anti-reflection coating may be applied to one or both of the joining surfaces 122 and 124. The use of an anti-reflection coatings 120, and coated surfaces 122 and 124 is beneficial since it reduces the extraneous light reflected from the internal surfaces of the lens. A thin, highly pigmented, opaque layer 126 of material may be applied over the junction to mask out the rays which would otherwise cause reflections.

FIG. 10 illustrates two hydrogel lenses which represent lenses 130 and 132 to be used in the right and left eyes of a user. In this embodiment, the lens elements 142a–142c for the left eye have powers respectively corresponding to the powers of lens elements 144a–144c for the right eye. This too, is to facilitate the adaptation process.

Figure 11:
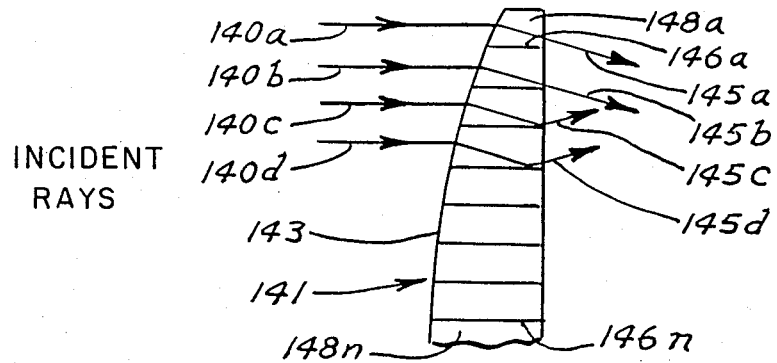
Figure 12:
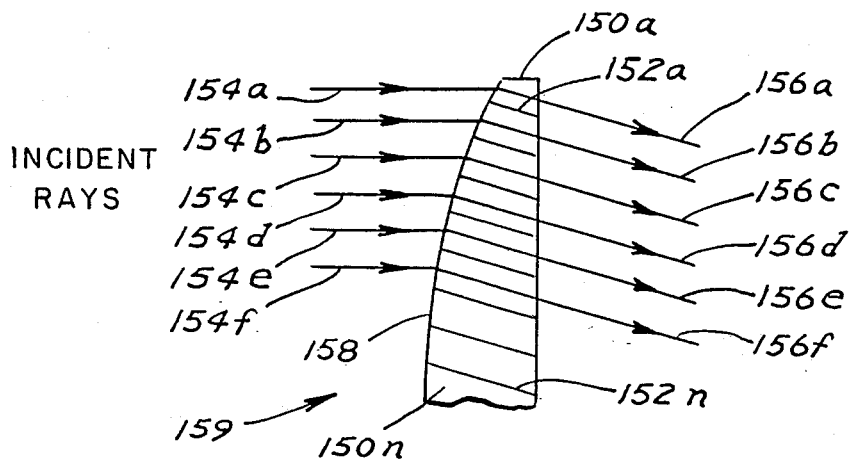
Figure 13:
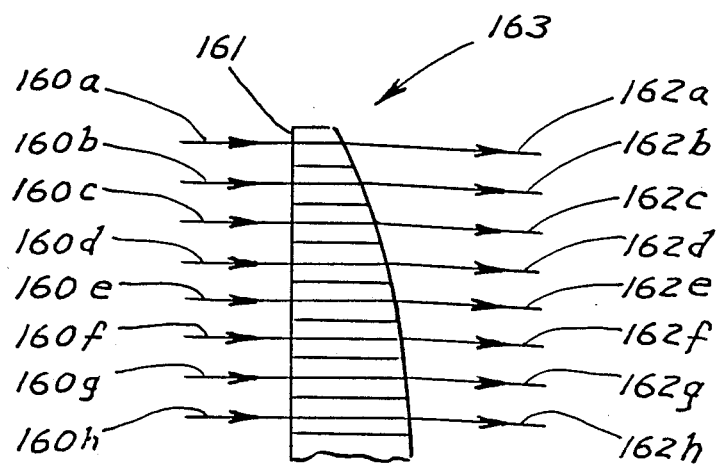

FIGS. 11, 12 and 13 illustrate sectional views through hydrogel lenses having a large number of elements. In a lens, such as hydrogel lens 10, having the incident rays 140a-140d entering the convex side 143, of a lens 141, a potential problem arises due to the fact that the incident rays are diffracted inwardly forming diffracted rays 145a-145d and may strike portions of the inner wall 146a-146n of the concentric elements 148a-148n causing an unwanted reflection and distortion. The incident rays which are close to the inner periphery of the annular elements 148a-148n will be diffracted in the direction of the junction as shown by the rays 145c and 145d. The rays 145a and 145b, which fall further from the inner periphery, will not strike the corresponding wall 146a-146n. This situation where incident rays, such as 140c and 140d, are reflected can lead to annoying ghosting and distortion.

In FIG. 12, the concentric annular elements 150a-150n have walls 152a-152n which are angled causing incident rays 154a-154f to be diffracted into diffracted rays 156a-156f which are essentially parallel to the concentric annular elements 150a-150n, thereby reducing the tendency to cause reflections when entering the convex side 158 of the lens 159. If further reduction in reflections are desired the surface area near the junctions can be masked as previously described.

In FIG. 13, the incident rays 160a-160n strike the plano surface 161 of lens 163. Since there is very little diffraction at this surface, reflections are largely avoided and diffracted rays 162a-162n are diffracted minimally to depart the lens posterior at only a slightly diffracted angle. As in the case with the embodiment of FIG. 12, reflections can be further reduced by masking the surface area in the region of the junctions between segments.

MODE OF OPERATION

In the case where a defective natural lens is to be replaced, it is customary to make extensive measurements on the eye prior to the removal of the defective natural lens and its replacement with a fixed focus implantable lens. Such measurements allow the selection of a lens having appropriate power for the individual and the nominal distance to the object which is desired to be brought into focus on the retina. This approach to the problem has the disadvantage that a wide range of powers must be available to the surgeon. Since each lens is individually fabricated, the economic burden of fabricating a wide variety of powers adds substantially to the cost of lenses. It would be much cheaper to manufacture only a few lenses and use them in all patients. The cost of manufacture would be reduced and inventory requirements would be much less burdensome.

The use of flexible hydrogel material allows the lens to be folded or rolled up and inserted into the eye through an incision or puncture which is much smaller than required for a conventional, rigid lens. Since the insertion procedure is simplified, the cost of implantation is reduced and the chance for success is enhanced.

Reduction of the cost of the lenses would have the effect of increasing the availability of this procedure to those who currently lack the economic means to afford such an operation. This is particularly the case in third world countries where costs are often the overriding consideration in medical care.

Various modifications can be made to the present invention without departing from the apparent scope herein.

I claim:
1. A zone of focus hydrogel lens for use with an eye comprising:
   a. a cylindrical optical hydrogel element;
   b. at least one annular optical hydrogel element joined with said cylindrical element to form a unitary lens structure having a front surface, a rear surface and a circular periphery;
   c. each of said hydrogel elements serving to create an image on a distinct portion of the retina; and,
   d. at least two of said hydrogel elements having different powers whereby objects at different distances from the eye are simultaneously brought to a focus on distinct portions of the retina; and,
   (d) at least two of said lens elements are of different colors.

2. A lens according to claim 1 wherein at least two of said elements are of hydrogel materials having different indices of refraction.

3. A lens according to claim 1 wherein at least two of said elements have different surface curvature.

4. A lens according to claim 3 further including a layer of transparent material overlying one of said front and rear surfaces to provide a smooth surface thereon.

5. A lens according to claim 3 further including first and second layers of transparent material overlying said front and rear surfaces, respectively, to provide smooth surfaces thereon.

6. A lens according to claim wherein the boundaries between said elements include an anti-reflection material.

7. A lens according to claim 1 wherein the surface area of the boundaries between said elements are masked with an opaque material to block passage of rays which would otherwise cause reflections.

8. A lens according to claim 1 wherein said elements are joined with a transparent adhesive material.

9. A lens according to claim 8 wherein said adhesive material includes an anti-reflection additive.

10. A lens according to claim 1 wherein said elements are joined during an extrusion process.

11. A lens according to claim 1 wherein adjacent said elements have different indices of refraction.

12. A lens according to claim 1 comprised of elements each having different indices of refraction.

13. A lens according to claim 12 consisting of three elements.

14. A lens according to claim 1 having at least three elements.

15. A lens according to claim 1 wherein the front surface area of said annular element is greater than the front surface area of said cylindrical element.

16. A lens according to claim 1 wherein said elements providing sharp focus images of near objects are positioned within the inner half of the lens.

17. First and second lenses according to claim 1 for use in left and right eyes wherein like power elements are similarly positioned.

18. A lens according to claim 1 having a planar front surface and a convex rear surface to reduce internal reflections.

19. A lens according to claim 18 wherein the surface areas of the boundaries between said elements are masked with an opaque material to block passage of rays which would otherwise cause reflections.

* * * * *